United States Patent [19]

Herlyn

[11] Patent Number: 5,854,069
[45] Date of Patent: Dec. 29, 1998

[54] GD2 ANTI-IDIOTYPIC ANTIBODIES AND USES THEREOF

[75] Inventor: Dorothee Herlyn, Wynnewood, Pa.

[73] Assignee: The Wistar Institute of Anatomy & Biology, Philadelphia, Pa.

[21] Appl. No.: 844,073

[22] Filed: Apr. 18, 1997

Related U.S. Application Data

[60] Provisional application No. 60/015,900 Apr. 22, 1996.
[51] Int. Cl.$^6$ .......................... A61K 39/395; C07K 16/42; C12N 5/12
[52] U.S. Cl. .......................... 435/327; 435/328; 435/354; 424/131.1; 424/136.1; 424/141.1; 424/278.1; 424/698; 424/133.1; 514/8; 530/387.2; 530/387.3
[58] Field of Search ...................................... 435/326, 327, 435/346, 328, 354; 530/388.1, 387.1, 387.2, 387.3; 424/131.1, 136.1, 141.1, 278.1, 698; 514/8

[56] References Cited

U.S. PATENT DOCUMENTS

| | | |
|---|---|---|
| 4,849,509 | 7/1989 | Thurin et al. . |
| 5,419,904 | 5/1995 | Irie . |
| 5,612,030 | 3/1997 | Chatterjee et al. .................. 424/131.1 |
| 5,653,977 | 8/1997 | Saleh .................................... 424/131.1 |

FOREIGN PATENT DOCUMENTS

| | | |
|---|---|---|
| WO 88/02117 | 3/1988 | WIPO . |
| WO 94/16731 | 4/1994 | WIPO . |
| WO 97/34634 | 9/1997 | WIPO . |

OTHER PUBLICATIONS

Cheung, NK, et al., Int. J. Cancer 54:499–505, 1993.
A. Hastings et al, "Production and Characterization of a Murine/Human Chimeric Anti–Idiotype Antibody that Mimics Ganglioside", *Cancer Research*, 52:1681–1686 (Apr. 1, 1992).
M. Riggott et al, "Anti–Idiotypic Monoclonal Antibodies to GM1 Identify Ganglioside Binding Proteins", *Glycobiology*, 6(6):581–589 (1996).
D. Herlyn et al., "Radioimmunodetection of Human Tumor Xenografts by Monoclonal Antibodies", *Cancer Res.*, 43:2731–2735 (1993).
R. Saxton et al., "Anti–Idiotype Antibody to Human Monoclonal L72 has Internal Image of Melanoma Ganglioside GD2", 78$^{th}$ Annual Meeting of the American Association for Cancer Research, Altanta, Georgia, May 20–23, 1987, *Proc. Am. Cancer Res. Annu. Meet.*, 28:389 (1987).
Herlyn et al., "Primary Melanoma Cells of the Vertical Growth Phase: Similarities to Metastatic Cells" *J. Natl. Cancer Instit.*, 74:283–289, 1985.
Herlyn et al., "Immunomodulatory Activity of Monoclonal Anti–Idiotypic Antibody to Anti–Colorectal Carcinoma Antibody CO17–1A in Animals and Patients" *J. Immunother.*, 15:303–311, 1994.
Mark et al., "Humanization of Monoclonal Antibodies", *The Handbook of Experimental Pharamcology*, vol. 113, Chapter 4, pp. 105–134, Springer–Verlag, Jun., 1994.
Koprowski et al., "Study of Antibodies Against Human Melanoma Produced by Somatic Cell Hybrids", *Proc. Natl. Acad. Sci. USA*, 75:3405–3409, 1978.
Gilles et al., "High–Level Expression of Chimeric Antibodies Using Adapted cDNA Variable Region Cassettes" *J. Immunol. Meth.*, 125:191–202 1989.
Koido et al., "Induction of Immunity to Colon Carcinoma Antigen CO17–1A by Monoclonal Anti–Idiotype (Ab2): Effects of Ab2 Fragmentation, Carrier and Adjuvant" *J. Tumor Targeting*, 1:115–124, 1995.
Anderson et al., "Idotype Network Responses to Murine Immunoglobulin G3 Anti–Carbohydrate Antibodies", *J. Immunotherapy*, 11:267, 1992.
Saleh et al., "Generation of a Human Anti–Idiotypic Antibody that Mimics the GD2 Antigen" *J. Immunol.*, 151(6):3390–3398, Sep. 1993.
Roitt et al., "Anti–Idiotypes as Surrogate Antigens: Structural Considerations" *Immunol. Today*, 6:265–267, 1985.
J. of Immunology, Sep. 1993, vol. 151, pp. 3390–3398, Saleh et al., "Generation of Human Anti–Idiotypic Antibody that Mimics the GD2 Antigen".
Cancer Immunol Immunother, 1993, vol. 36, pp. 281–292, Irvine et al., "Induction of Delayed–Type Hypersensitity Responses by Monoclonal Anti–Idiotypic to Tumor Cells Expressing Carcinoembryonic Antigen and Tumor–Associated Glycoprotein–72".
European J. of Cancer, 1995, vol. 31A, pp. 261–267, Handgretinger et al., "A Phase I Study of Human/Mouse Chimeric Antiganglioside GD2 Antibody ch14.18 in Patients with Neuroblastoma".
1 pp. abstract of Japanese Patent 5,0330,991, Feb. 9, 1993.

*Primary Examiner*—Christina Y. Chan
*Assistant Examiner*—Mary B. Tung
*Attorney, Agent, or Firm*—Howson and Howson

[57] ABSTRACT

Three murine monoclonal anti-idiotype antibodies which functionally mimic GD2 are described. These antibodies are useful in compositions for inducing a CD4 T cell response to cancers characterized by high density GD2 expression and in the diagnosis of high density GD2 expression.

19 Claims, 12 Drawing Sheets

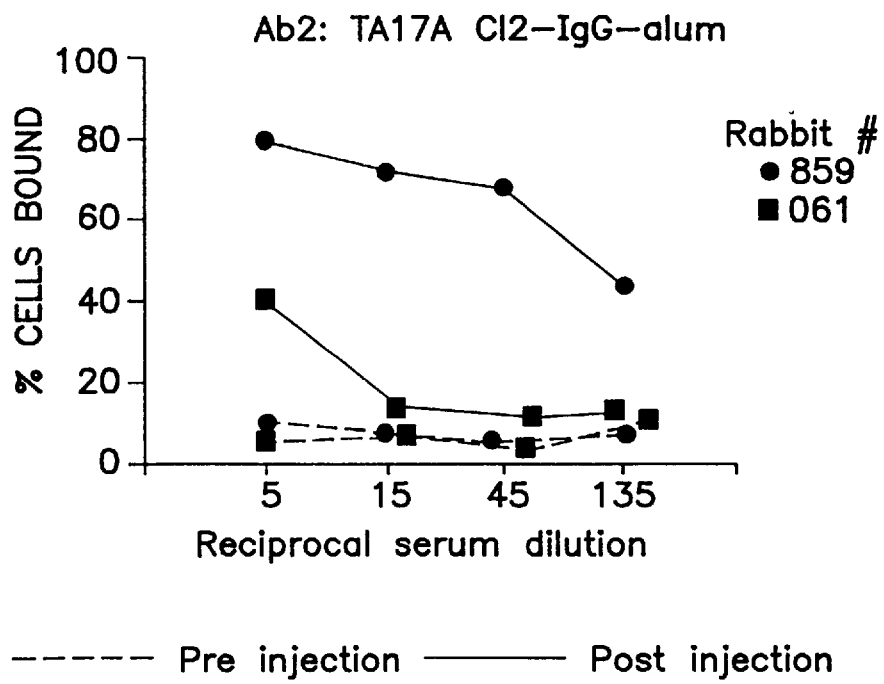
FIG. IA
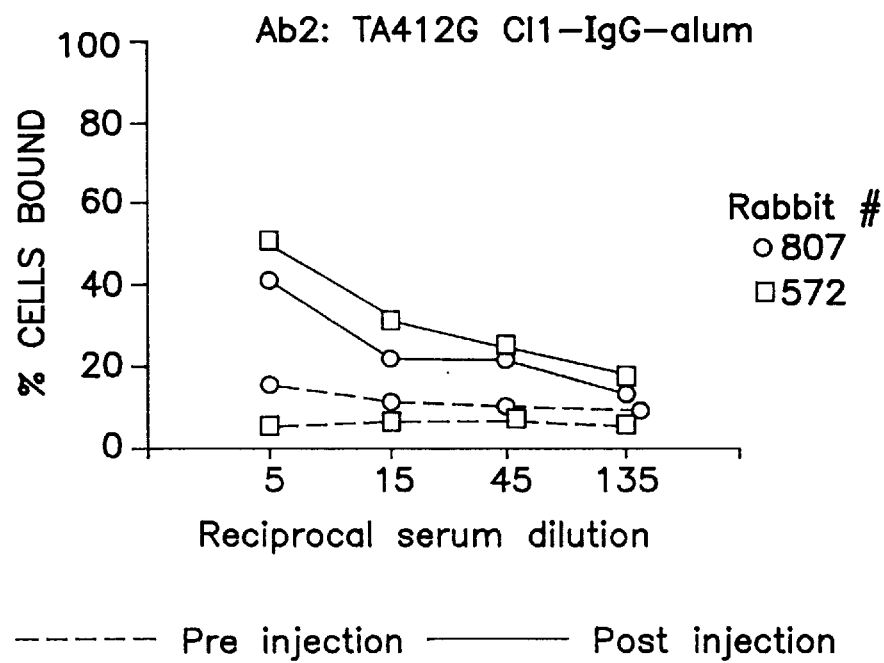
FIG. IB

GD2 ANTI-IDIOTYPIC ANTIBODIES AND USES THEREOF

This invention was made under work supported by National Institutes of Health, Grant No. CA60595. The United States Government has certain rights in this invention.

CROSS-REFERENCE TO RELATED APPLICATION

This application claims priority of U.S. Provisional patent application No. 60/015,900, filed Apr. 22, 1996.

1. Field of the Invention

This invention relates generally to immunomimetic molecules, and more particularly to anti-idiotypic antibodies.

2. Background of the Invention

Tumor-associated antigens are frequently expressed during normal fetal ontogeny and/or may be present on normal cells [M. N. Saleh et al, *J. Immunol.*, 151(6):3390–3398 (Sep. 15, 1993)]. Consequently, the host is usually tolerant to such antigens and does not generate an effective antitumor immune response. One approach to stimulate an antitumor immune response to such antigens is the use of immunomimetic molecules that mimic tumor-associated antigens and can be used as vaccines [I. Roitt et al, *Immunol. Today*, 6:265 (1985)]. Anti-idiotype (anti-Id or Ab2) antibodies that react with the binding site of antibodies directed at tumor-associated antigens may mimic the corresponding tumor-associated antigen. Such "internal image" anti-Ids have been shown to resemble various antigens and elicit specific immune responses in animal models.

Gangliosides are a class of carbohydrate-rich glycolipids of extremely large size and complexity, which are usually found on the outer surface of cell membranes, especially among the cells of the nervous system. GD2 is present in central nervous tissue, in melanomas, gliomas, neuroblastoma, and small cell lung carcinoma at high density. In general, ganglioside antigen GD2 occurs primarily in primary and metastatic melanoma and is less abundantly present in normal tissue.

M. N. Saleh et al, cited above, describe the generation of a human anti-Id antibody that mimics the glycolipid GD2 and elicits both a humoral and cellular immune response in preclinical animal studies. However, attempts to develop murine anti-Id reagents that mimic the GD2 antigen and elicit an anti-GD2 immune response have proven difficult [D. R. Anderson and R. E. McCoobery, *J. Immunother.*, 11:267 (1992)].

What are needed are anti-Id antibodies which mimic the paratope of the GD2.

Summary of the Invention

The present invention provides three murine monoclonal anti-idiotype antibodies which are characterized by the ability to mimic ganglioside GD2 function and which induce CD4+ T cell responses. The three antibodies are designated herein as TA17A Cl2, TA412G Cl1 and TB310B Cl1. Also provided herein are fragments of these antibodies.

In one aspect, the invention provides an immunogenic composition useful in eliciting a CD4-mediated cellular immune response, wherein the composition contains at least one of the above-identified anti-idiotype antibodies.

In another aspect, the invention provides a method of eliciting CD4+ T cells in an animal by administering to the animal a composition containing at least one of the murine anti-idiotype antibodies of the invention.

In yet another aspect, the invention provides a method of treating a tumor characterized by GD2 expression by administering to the animal a composition containing one or more of the anti-Id antibodies of the invention.

In still another aspect, the invention provides a method of detecting a tumor characterized by GD2 expression in a biological sample.

Other aspects and advantages of the present invention are described further in the following detailed description of the preferred embodiments thereof.

BRIEF DESCRIPTION OF THE DRAWINGS

FIG. 1A is a line graph illustrating binding to melanoma cells WM164 of Ab3 elicited by alum precipitated Ab2 TA17A Cl2 IgG.

FIG. 1B is a line graph illustrating binding to melanoma cells WM164 of Ab3 elicited by alum precipitated Ab2 TA412G Cl1 (B).

DETAILED DESCRIPTION OF THE INVENTION

Figure 1C:
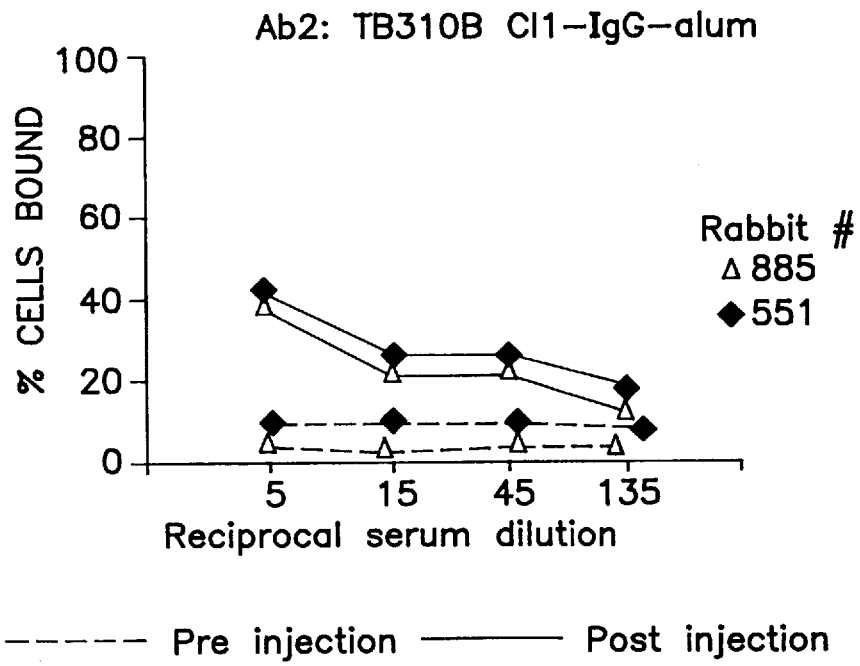
FIG. 1C is a line graph illustrating binding to melanoma cells WM164 of Ab3 elicited by alum precipitated Ab2 TB310B Cl1 IgG.

The present invention provides three monoclonal murine anti-idiotype (Ab2) antibodies, characterized by the ability to induce $CD4^+$ T cell activity. These antibodies are expected to be useful in treating tumors characterized by GD2 expression.

The monoclonal Ab2, an IgG2a isotype, of the invention is produced by culturing the murine hybridoma cell line, designated TA17A Cl2. This cell line was deposited with the American Type Culture Collection (ATCC), 10801 University Boulevard, Manassas, Va. 20110-2209 (U.S.A.) on Apr. 12, 1996, pursuant to the Budapest Treaty and was granted accession number HB-12083.

A second monoclonal Ab2, an IgG2b isotype, of the invention is produced by culturing the murine hybridoma cell line, designated TA412G Cl1. This cell line was deposited with the ATCC on Apr. 12, 1996, pursuant to the Budapest Treaty, and was granted accession number HB-12084.

A third monoclonal Ab2, an IgG2b isotype, of the invention is produced by culturing the murine hybridoma cell line, designated TB310B Cl1. This cell line was deposited with the ATCC on Apr. 12, 1996, pursuant to the Budapest Treaty, and was granted accession number HB-12085.

As described in more detail below, for production of these Ab2, mice were immunized with ME361, an anti-CD2 monoclonal antibody (Ab1). Mice that were seropositive for Ab2 were boosted with ME361 three days prior to fusing to their splenocytes to produce hybridomas using standard techniques. The Ab2 were characterized in vitro, injected into rabbits, and the anti-anti-idiotypes (Ab3) induced in rabbits were analyzed for binding. The Ab2 described herein functionally mimic GD2, both in vitro and in vivo, in experimental animals.

The Ab2 antibodies described herein can be lyophilized for storage and reconstituted in a suitable carrier prior to use. This technique has been shown to be effective with conventional immunoglobulins. Known lyophilization and reconstitution techniques can be employed.

The invention further encompasses functional fragments of the Ab2 of the invention, including, Fab, $F_v$, and $F(ab')_2$ fragments, synthetic molecules containing the binding site of the Ab2 of the invention, and the complementarity determining regions (CDRs). Further, these functional fragments may be used in the production of recombinant antibodies, including bifunctional antibodies, chimeric antibodies, and humanized antibodies, which preferably retain the antigen binding specificity of the Ab2 of the invention. Such recombinant antibodies may be constructed and produced according to known techniques [see, e.g., S. D. Gillies et al, *J. Immunol. Meth.*, 125:191–202 (1989); and G. E. Mark and E. A. Pladlan, "Humanization of Monoclonal Antibodies", *The Handbook of Experimental Pharmacology*, Vol. 113, Chapter 4, pp. 105–133, Springer-Verlag (June, 1994)]. These functional fragments and recombinant antibodies may be used for a variety of purposes, including any of those described herein for the Ab2.

Thus, the present invention provides an immunogenic composition or other pharmaceutical composition containing an effective amount of one or more Ab2 of the invention. These compositions are suitable for eliciting CD4+ T cells in an animal and treatment of tumors associated with GD2 expression, particularly tumors characterized by high density GD2 expression including melanomas.

Pharmaceutical formulations, including selection of appropriate adjuvants and carriers, are well known to those of skill in the art. Compositions of the invention may be prepared as pharmaceutical compositions containing an effective amount of at least one of the Ab2 antibody of the invention as an active ingredient in a nontoxic and sterile pharmaceutically acceptable carrier. For example, an aqueous suspension or solution containing an antibody, preferably buffered at physiological pH, in a form ready for injection is preferred. The compositions for parenteral administration will commonly comprise a solution of an antibody of the invention and selected adjuvant dissolved in an acceptable carrier, preferably an aqueous carrier.

A variety of aqueous carriers may be employed, e.g., 0.4% saline, 0.3% glycine, and the like. These solutions are sterile and generally free of particulate matter. These solutions may be sterilized by conventional, well known sterilization techniques. The compositions may contain pharmaceutically acceptable auxiliary substances as required to approximate physiological conditions such as pH adjusting and buffering agents, etc.

Additionally, although a therapeutic composition containing the single anti-idiotype antibody reagent (or a recombinant antibody derived therefrom) is desirable, optionally, a composition of the present invention may include other active ingredients. Particularly desirable ingredients are one or more selected adjuvants. Among such adjuvants are included, without limitation, aluminum hydroxide (alum), BCG (Bacille Calmette Guerin), DETOX, SAF-1, muramyl dipeptide (MDP), liposomes containing Lipid A, and ISCOMS. Other conventional adjuvants such as saponins (Quil A, QS21) may also be useful.

Such pharmaceutical compositions contain an effective amount of the Ab2. By "effective amount" is meant about 1 μg to 10 mg, and preferably about 4 mg antibody per ml carrier, e.g., saline or phosphate buffered saline, and adjuvant per injection.

Suitably, a pharmaceutical formulation of the invention may be administered by any suitable route which delivers the agent to the host. The pharmaceutical compositions of the invention are particularly useful for parenteral administration, i.e., subcutaneously, intradermally and intramuscularly.

Thus, a pharmaceutical composition of the invention for subcutaneous or intradermal injection could be prepared to contain 1 mL sterile buffered water or saline, and about 1 μg to 10 mg of an antibody of the invention and adjuvant. Actual methods for preparing parenterally administrable compositions are well known or will be apparent to those skilled in the art and are described in more detail in, for example, Remington's Pharmaceutical Science, 15th ed., Mack Publishing Company, Easton, Pa.

Once formulated, a composition's administration is based upon patient and clinical factors that are well appreciated by those of skill in the art. Thus, the present invention further provides a method of administering to an animal an immunogenic or pharmaceutical composition of the invention. This composition is particularly useful in treating cancers associated with abundant GD2 expression, including melanoma, glioma, neuroblastoma, and small cell lung carcinoma. The composition may be administered in multiple doses. Suitable dosage regimens can readily be determined, and adjustments made, by those of skill in the art.

It is preferred that the therapeutic agent of the invention, when in a pharmaceutical preparation, be present in unit dose forms. The appropriate therapeutically effective dose can be determined readily by those of skill in the art. Such dose may, if necessary, be repeated at appropriate time intervals selected as appropriate by a physician. It is preferable that the composition be administered at an optimal dosage of about 1 mg to about 4 mg per injection, and most preferably about 1 mg Ab2/ml/injection. In one embodiment, at least four to six doses are administered, generally at one or two week intervals. The number of repeated dosages is dependent on the level of immune response in the individual patient. Desirably a booster may be administered when antibody titer drops to below 1:500 serum dilution. Additionally the immune response may be measured by the induction of antigen specific T cells.

The invention further provides a method of eliciting $CD4^+$ T cells in an animal and a method of treating a tumor, particularly a solid tumor, characterized by GD2 expression. These methods involve administration of an effective amount of a pharmaceutical composition of the invention to the animal. Suitable doses and treatment regimens are discussed above.

The Ab2 antibodies of this invention may also be used in standard assay formats for the diagnosis of tumors expressing GD2 and for tracking progress of treatment of the disease. Desirably, the Ab2 and functional fragments thereof, are conventionally labelled for use in ELISAs, immunofluorescence, and other conventional assay formats for the measurement of GD2 antigen in an appropriate biological sample. Suitable label systems are well known to those of skill in the art and include fluorescent compounds, radioactive compounds or elements, and a variety of enzyme systems. As used herein, suitable samples include, without limitation, whole blood, serum, plasma, tissue samples, bone marrow, and urine.

One such method, for example, involves contacting the biological sample with the labeled Ab1 under conditions which allow formation of complexes between Ab1 and GD2 in said biological fluid. The presence of such complexes between Ab1 and GD2 is demonstrated by the inhibition of binding of Ab1 to the immobilized Ab2. Detection methods, including labelling systems, are well known in the art.

The present invention also provides a kit for detecting GD2, or antibodies thereto, in a biological sample. Components of such a kit may be readily determined by those of skill in the art. For example, such a kit may include a supporting matrix on which the Ab2 is immobilized and a labeled Ab1 (e.g., a MAb to GD2). Suitable labels are as described above in connection with the method of the invention.

These examples provide methods for preparing and using the anti-Id antibodies of the invention. These examples are illustrative only and do not limit the scope of the invention.

EXAMPLE 1

Production of Anti-Idiotypes (Ab2)

A. Immunization with Ab1

Monoclonal antibody ME361 [U.S. Pat. No. 4,849,509] binds strongly to GD2 ganglioside and weakly to GD3 ganglioside. For production of monoclonal Ab2 to Ab1 ME361, BALB/c mice (Harlan Sprague Dawley, Indianapolis, Ind.), were immunized repeatedly s.c. with 20 $\mu$g of Ab1 ME361 F(ab')$_2$ [D. Herlyn et al, Cancer Res., 43:2731–2735 (1993)] coupled to keyhole limpet hemocyanin [Koido et al, J. Tumor Targeting, 1:115–124 (1995)] and emulsified in complete (first injection) or incomplete (subsequent injections) Freund's adjuvant.

B. Antibody Binding Assay

Presence of Ab2 in sera of mice immunized with Ab1 ME361 was determined in radioimmunoassay (RIA). Wells of microtiter plates were coated with ME361 F(ab')$_2$, followed by incubation of the wells with mouse Ab2-containing sera. Mouse Ab2 bound to the plates was detected by $^{125}$I-labeled goat anti-mouse Fc (Cappel Organon Teknika Corp., Durham, N.C.) which had been absorbed three times to an immunoaffinity column coupled with MAb ME361 to remove any residual antibody reactivity to constant region determinants ($CH_1$ domain) present in the F(ab')$_2$ target preparation.

C. Hybridoma Production

Mice that were seropositive for Ab2, as determined by the assay in B. above, were boosted with 20 $\mu$g of Ab1 ME361 F(ab')$_2$ i.v. three days before fusion of splenocytes. Splenocytes from mice that were seropositive for Ab2 were fused to SP2/O myeloma cells using polyethylene glycol-1500 (Boehringer, Mannheim, Germany) according to standard techniques [Koprowski et al, Proc. Natl. Acad. Sci. USA, 75:3405–3409 (1978)].

Using these techniques, three hybridomas, producing TA17A, TA412G, or TB310B were produced by fusing splenocytes of mice immunized with Ab1 ME361 to SP20 myeloma cells.

EXAMPLE 2

In Vitro Antibody Characterization

All assays have been described in detail previously. Briefly, inhibition of binding of one Ab2 to Ab1 by another Ab2 was determined in RIA using Ab1 ME361-F(ab')$_2$ (30 ng/well) as target, unlabeled Ab2 (100 ng/well) as inhibitor and $^{125}$I-labeled second Ab2 (5,000 cpm/well) as tracer.

Monoclonal mouse Ab2 TA17A Cl2 (IgG2a), TA412G Cl1 (IgG2b) and TB310B Cl1 (IgG2b) against Ab1 ME361 bound only to Ab1 ME361 (IgG2b), but not to unrelated MAb ME313 (anti-proteoglycan) which is of the same isotype as the Ab1 . Ab2 TA17A Cl2, TA412G Cl1 and TB310B Cl1 maximally inhibited binding of Ab1 ME361 to tumor cells between 50 and 90% (not shown).

EXAMPLE 3

Determining Internal Image Nature of Ab2

A valid criterion for the internal image nature of Ab2 is the demonstration of induction by Ab2 immunizations of antigen-specific Ab3 across species barriers (i.e., in a species different from the species of origin of Ab1). The Ab2, therefore, were injected into rabbits, and rabbit Ab3 were characterized.

A. Induction and Detection of Ab3

For induction of Ab3, rabbits (New Zealand White, Hare-Marland, Hewitt, N.J.) were immunized subcutaneously with 300 µg of monoclonal mouse Ab2 antibody in alum on day 0, followed by 100 µg of antibody in alum on days 15, 36 and 60. Control animals received normal mouse IgG instead of Ab2.

All assays for detection of Ab3 have been described [Herlyn et al, J. Immunother., 15:303–311 (1994)]. Briefly, binding of rabbit Ab3 to cultured tumor cells was determined in mixed hemadsorption assay (MHA) using, as indicator cells, sheep red blood cells (SRBC) sensitized with rabbit anti-SRBC antibody to which goat anti-rabbit IgG antibody had been bound to detect binding of rabbit antibodies to tumor cells.

Figure 1D:
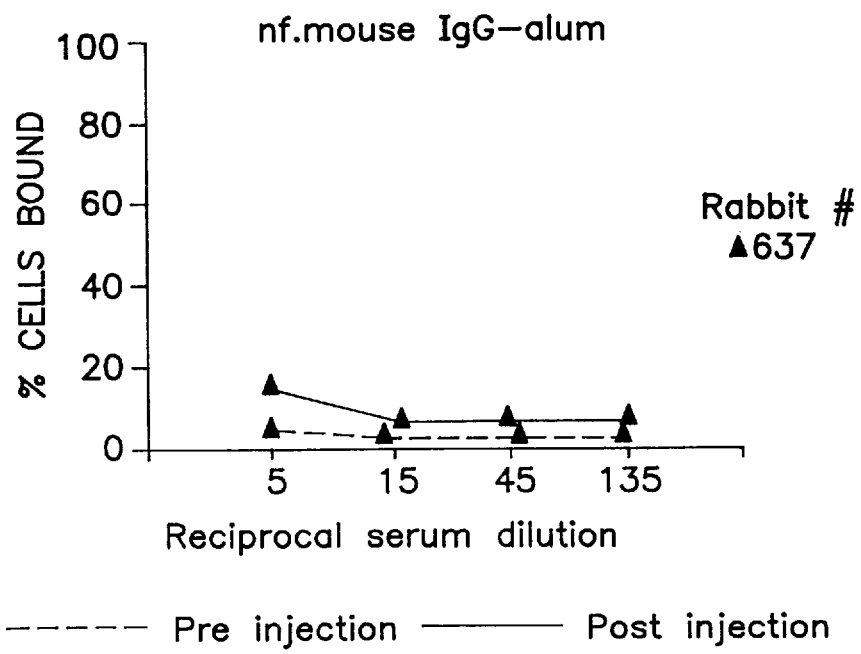
FIG. 1D is a line graph illustrating absence of significant binding of antibodies elicited by normal mouse IgG.
Figure 2A:
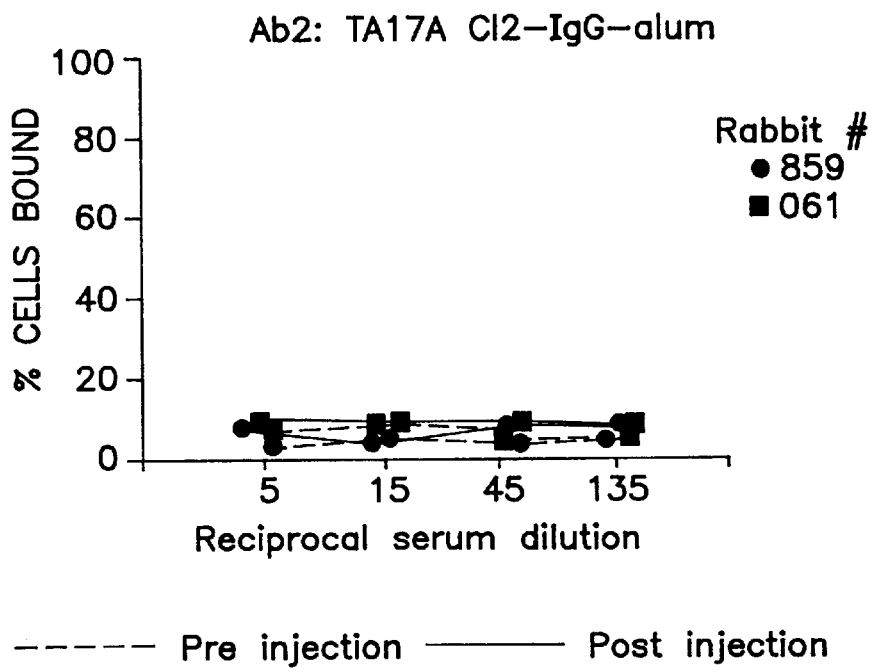
FIG. 2A is a line graph illustrating the absence of binding of rabbit Ab3 (anti-Ab2 TA17A) sera to colon carcinoma cells SW1116 in MHA.
Figure 2B:
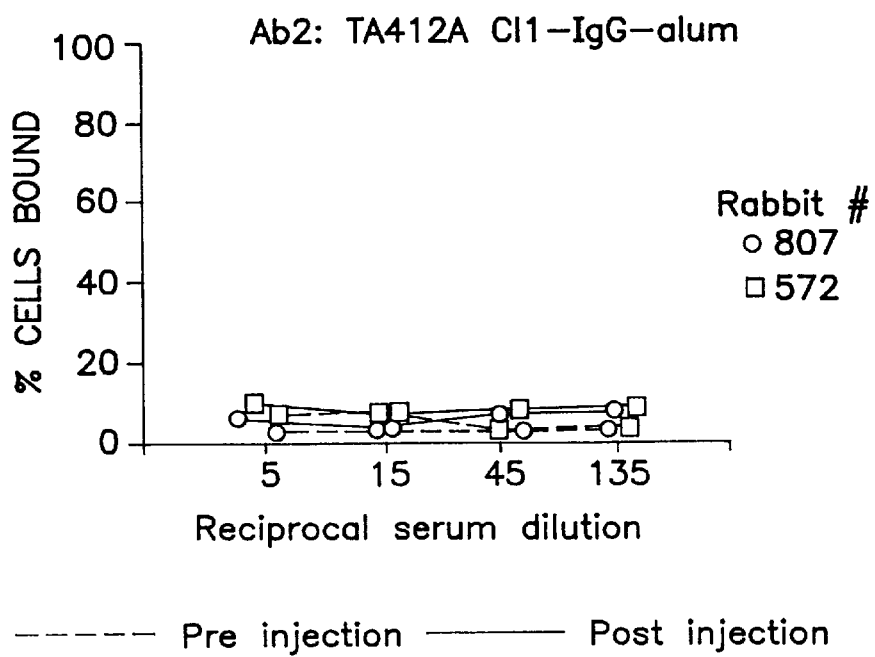
FIG. 2B is a line graph illustrating the absence of binding of rabbit Ab3 (anti-Ab2 TA412G) sera to colon carcinoma cells SW1116 in MHA.
Figure 2C:
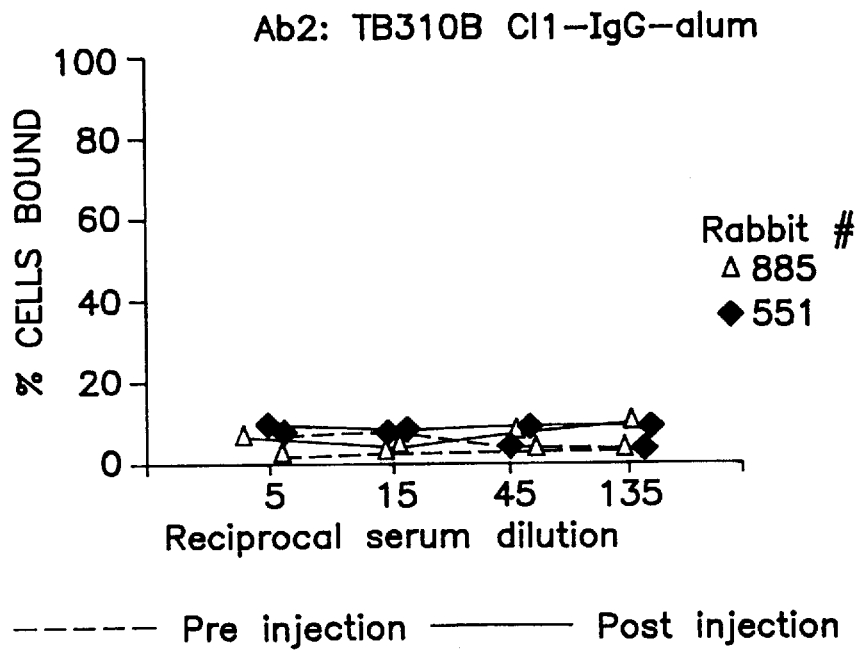
FIG. 2C is a line graph illustrating the absence of binding of rabbit Ab3 (anti-Ab2 TB310B) sera to colon carcinoma cells SW1116 in MHA.
Figure 2D:
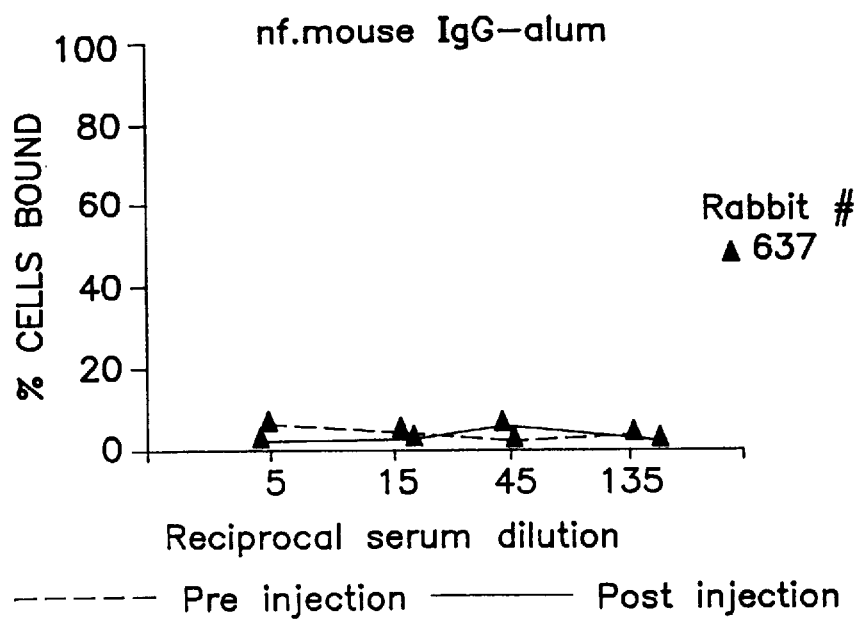
FIG. 2D is a line graph illustrating the absence of binding of rabbit antibodies elicited by normal mouse IgG1 to colon carcinoma cells SW1116 in MHA.
Figure 3A:
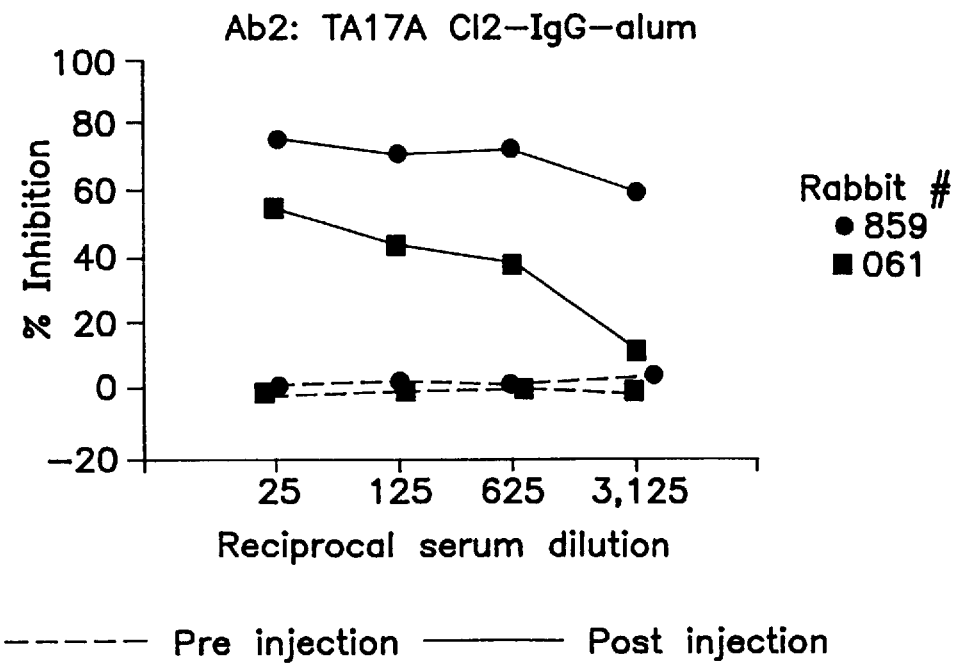
FIG. 3A is a line graph illustrating the inhibition of binding of Ab1 ME361 to WM164 melanoma cells by Ab3 elicited by Ab2 TA17A Cl2.
Figure 3B:
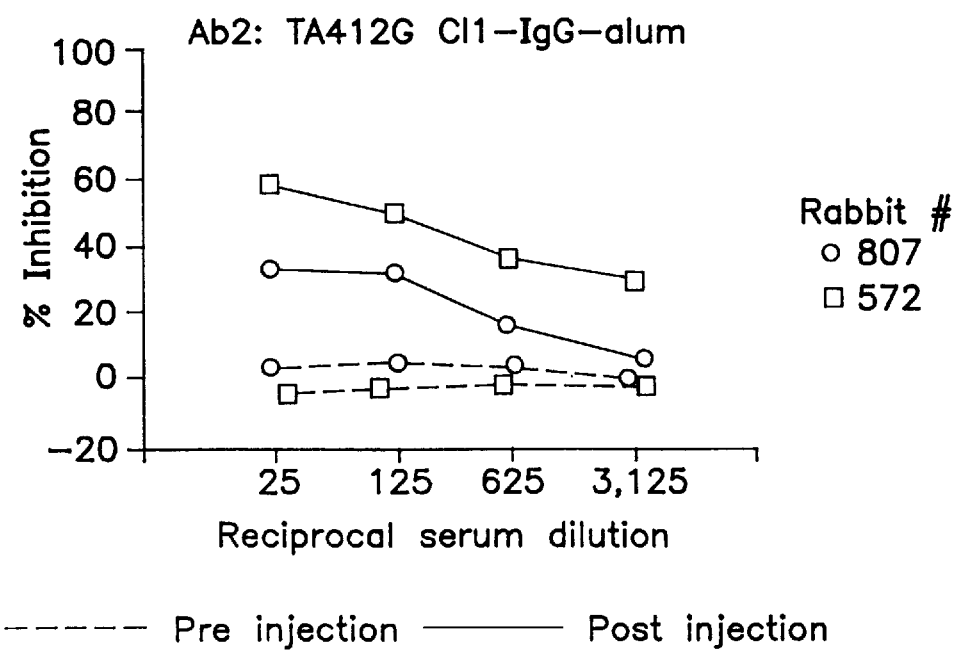
FIG. 3B is a line graph illustrating the inhibition of binding of Ab1 ME361 to WM164 melanoma cells by Ab3 elicited by TA412G Cl1.
Figure 3C:
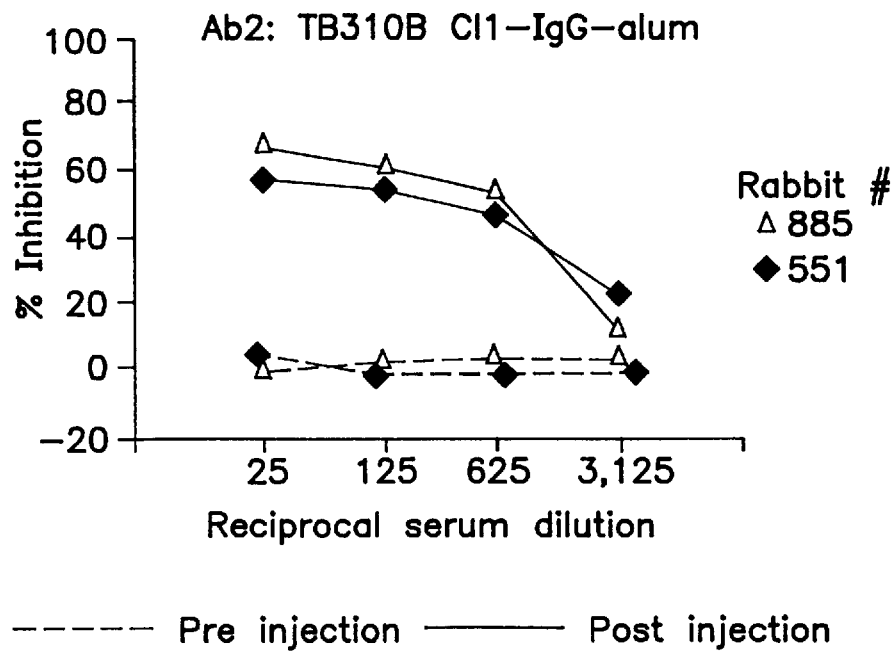
FIG. 3C is a line graph illustrating the inhibition of binding of Ab1 ME361 to WM164 melanoma cells by Ab3 elicited by TB310B Cl1.
Figure 3D:
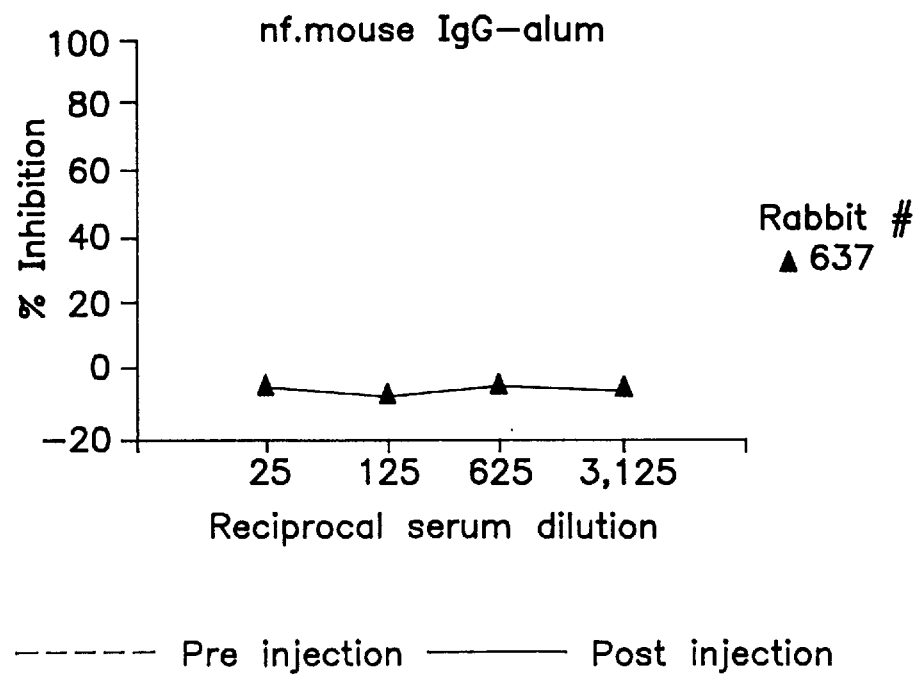
FIG. 3D is a line graph illustrating the absence of inhibition of binding of antibodies elicited by normal mouse IgG.
Figure 4A:
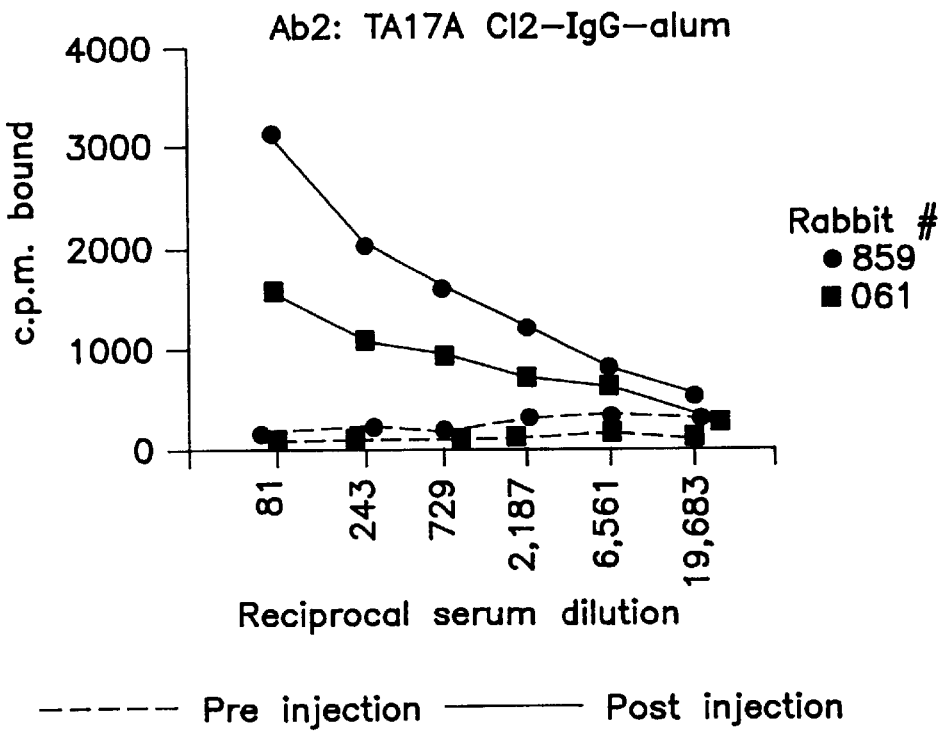
FIG. 4A is a line graph illustrating binding to GD2 antigen of Ab3 elicited by Ab2 TA17A Cl2.
Figure 4B:
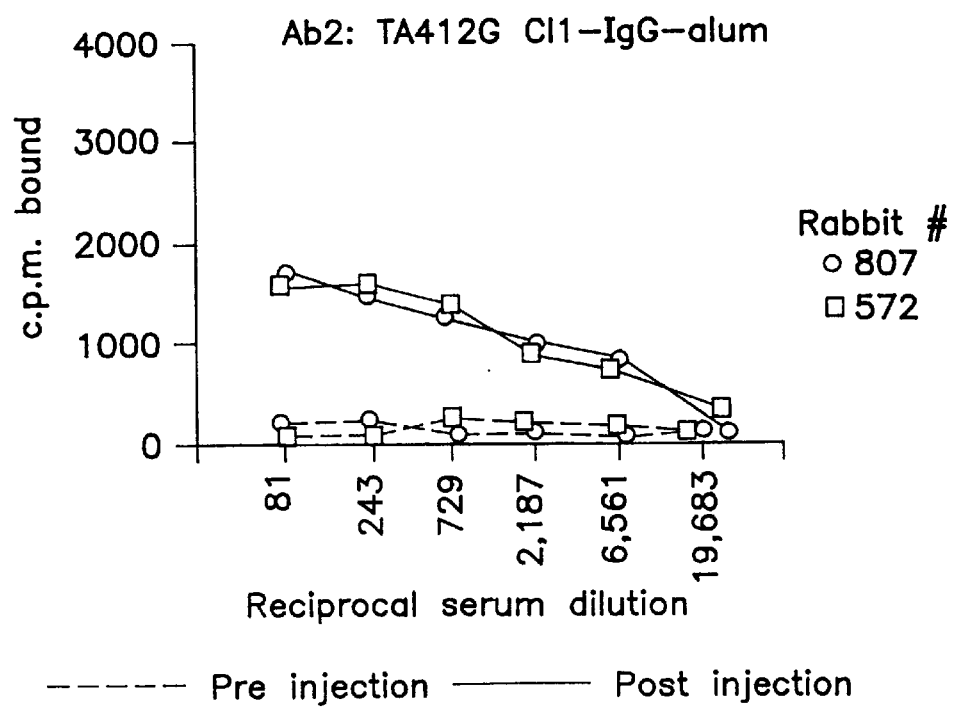
FIG. 4B is a line graph illustrating binding to GD2 antigen of Ab3 elicited by TA412G Cl1.
Figure 4C:
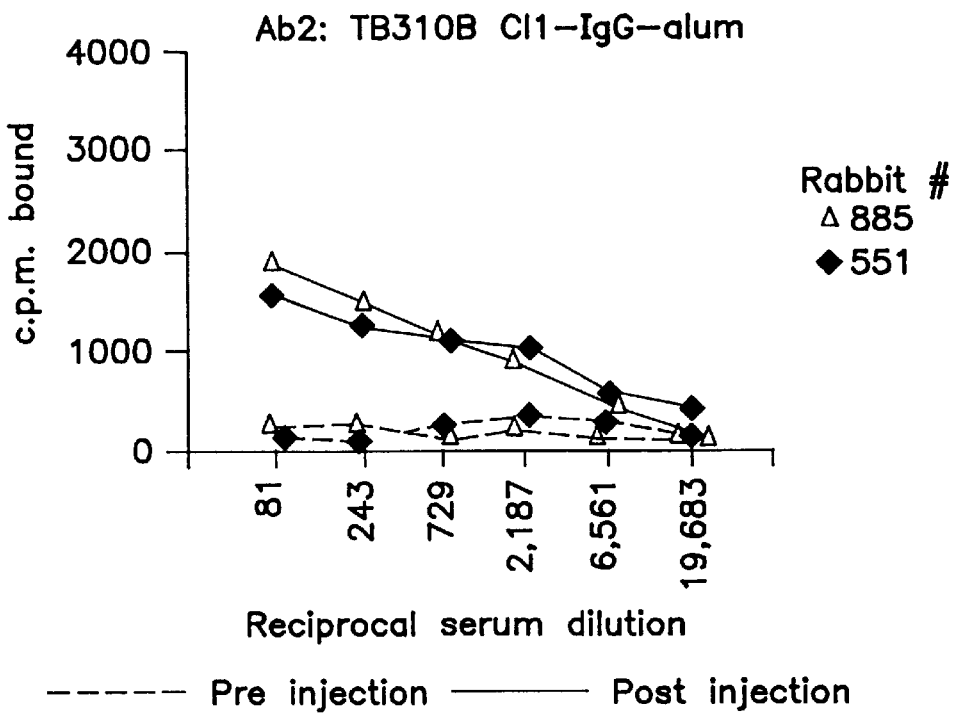
FIG. 4C is a line graph illustrating binding to GD2 antigen of Ab3 elicited by TB310B Cl1.
Figure 4D:
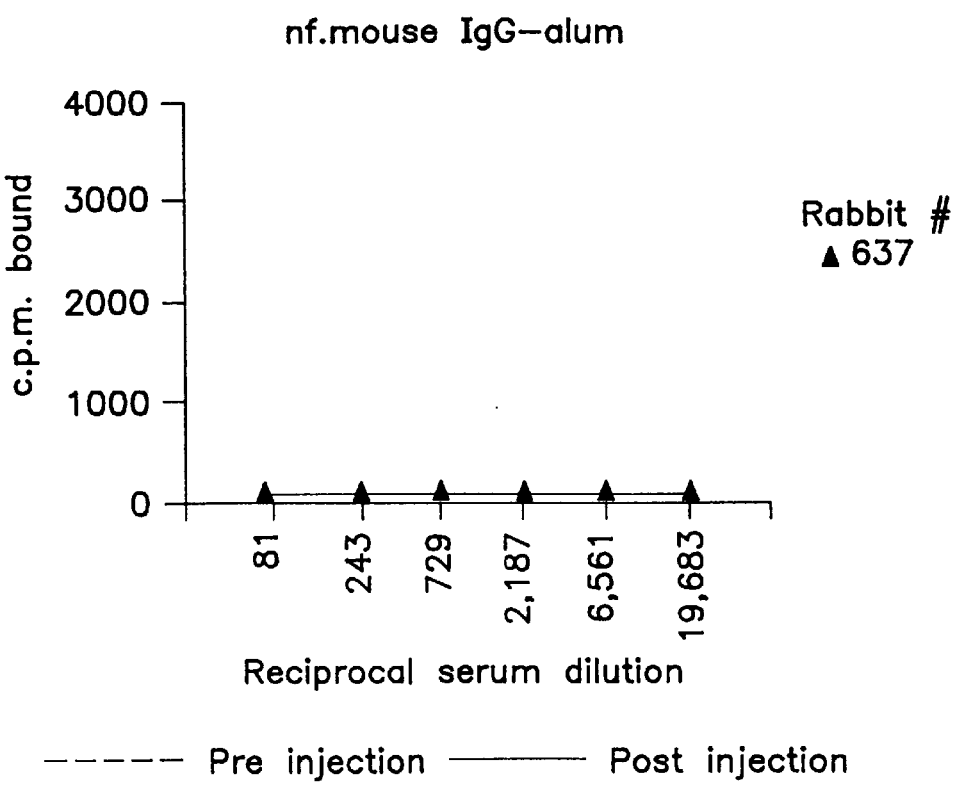
FIG. 4D is a line graph illustrating absence of significant binding to GD2 antigen of antibodies elicited by normal mouse IgG.
Figure 5A:
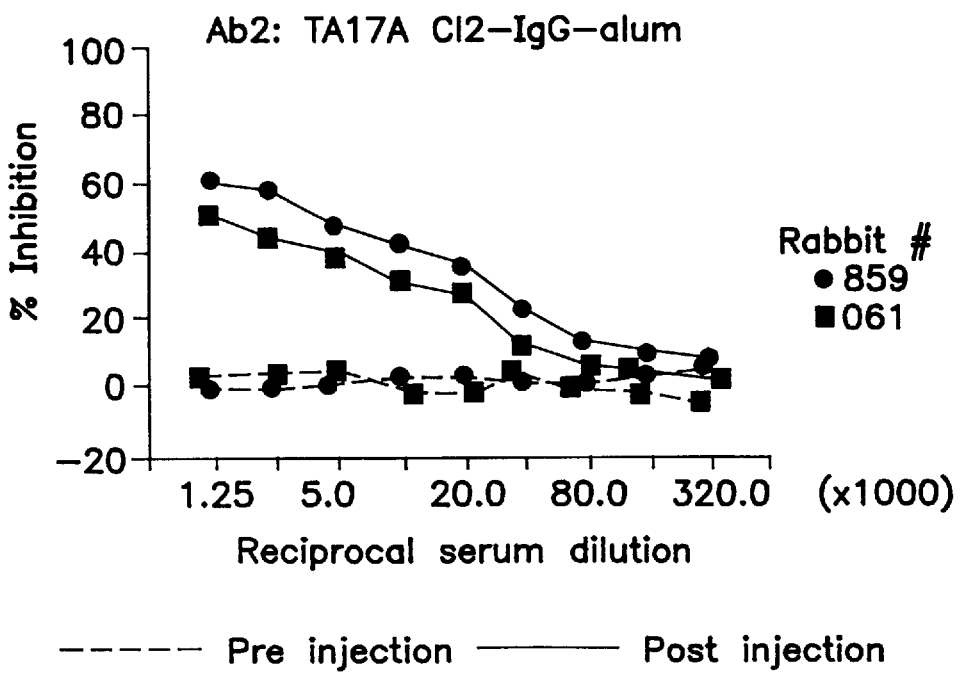
FIG. 5A is a line graph illustrating inhibition of binding of Ab1 to Ab2 by Ab3. Rabbits were immunized with Ab2 TA17A Cl2.
Figure 5B:
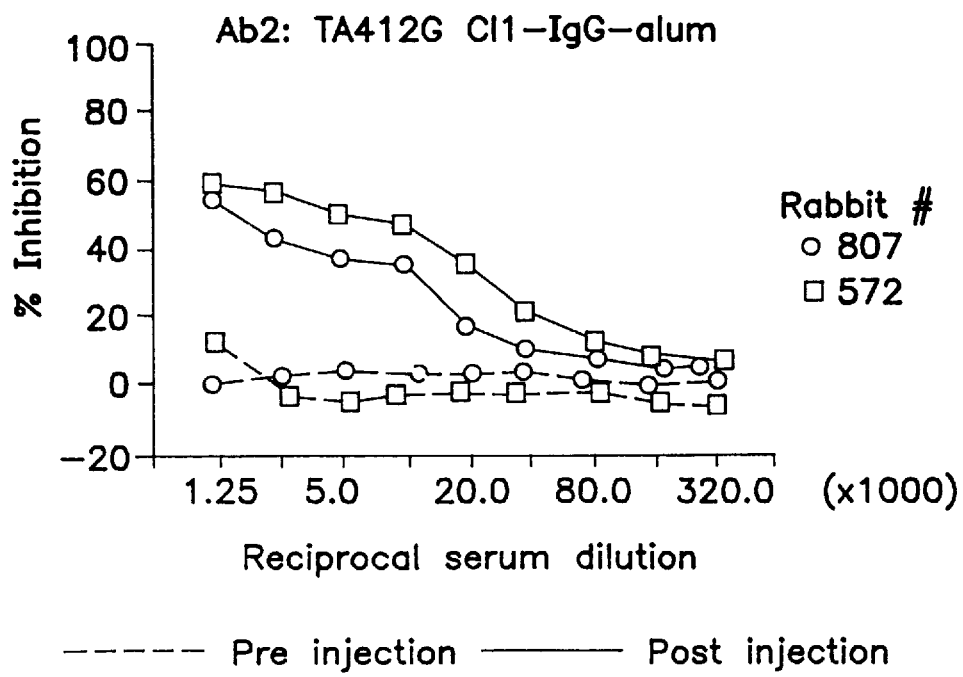
FIG. 5B is a line graph illustrating inhibition of binding of Ab1 to Ab2 by Ab3. Rabbits were immunized with Ab2 TA412G Cl1.
Figure 5C:
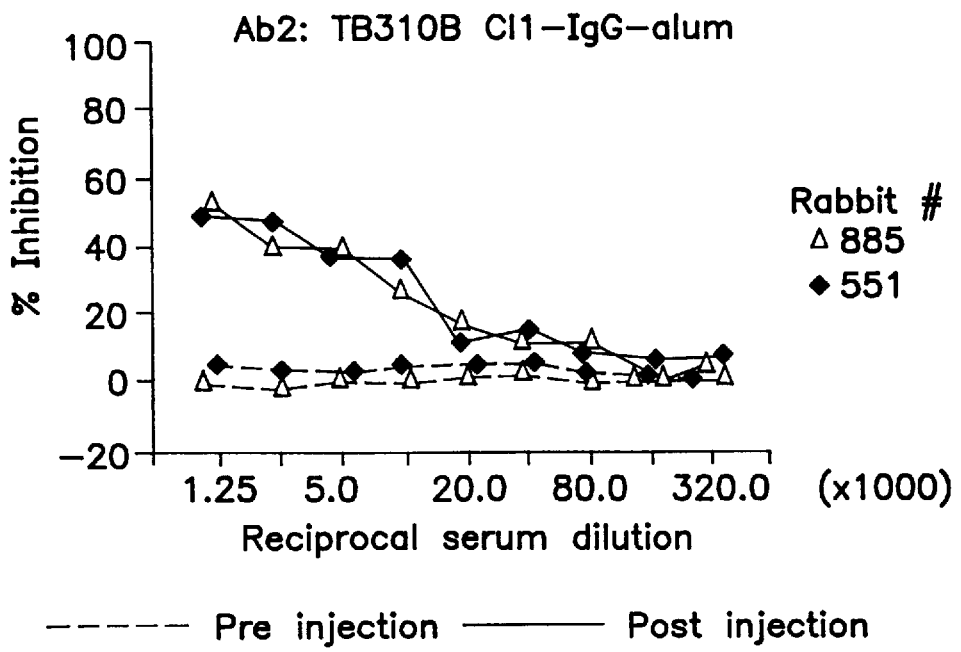
FIG. 5C is a line graph illustrating inhibition of binding of Ab1 to Ab2 by Ab3. Rabbits were immunized with Ab2 TB310B Cl1.
Figure 5D:
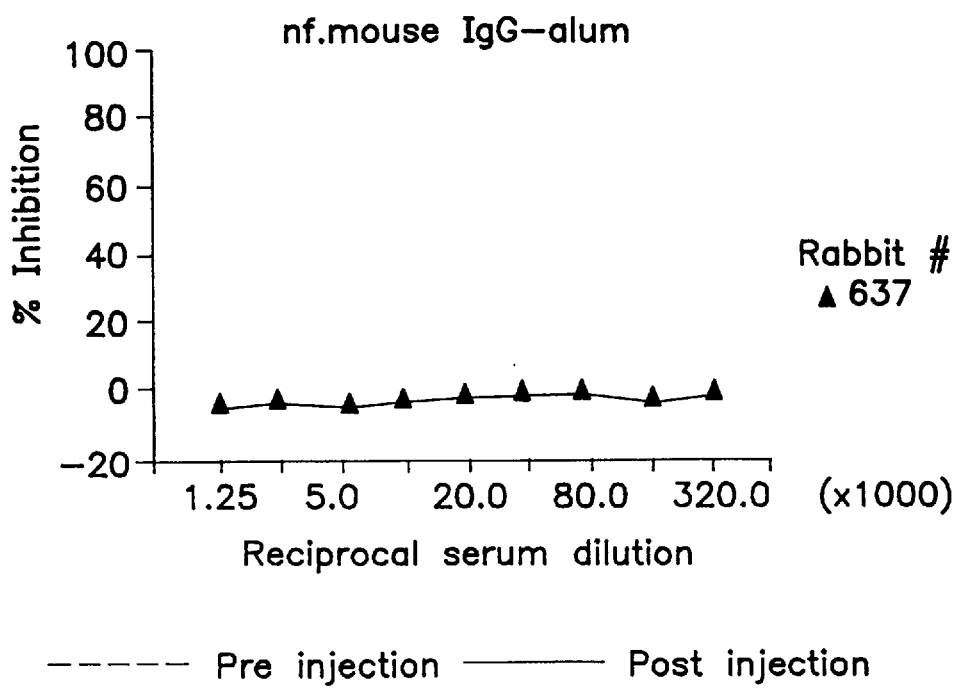
FIG. 5D is a line graph illustrating absence of significant inhibition of binding of Ab1 to Ab2 by Ab3. Rabbits were immunized with normal mouse IgG.

Ab3-containing sera from the two rabbits each immunized with Ab2 TA17A Cl2 (#859, #061), Ab2 TA412G Cl1 (#807, #572), or Ab2 TB310B Cl1 (#885 and #551) (post-immune sera diluted 1:25) bound significantly ($p<0.01$ as compared to control sera) to melanoma cells WM164 (FIG. 1), but not to antigen-negative CRC cells SW1116 (<5% of the cells maximally bound to Ab3-containing sera derived from both rabbits FIG. 2). Sera obtained from the same rabbits before immunization and sera from the rabbit (#637) immunized with normal mouse IgG did not bind significantly to melanoma cells (<5% of the cells maximally bound, FIG. 1). Ab3-containing sera from all six rabbits immunized with three different Ab2 significantly ($p<0.01$ as compared to control sera) and specifically inhibited the binding of Ab1 ME361 to melanoma cells (FIG. 3). Binding of unrelated anti-melanoma MAb J4 to melanoma cells not inhibited by the Ab3 sera (not shown).

Inhibition by rabbit Ab3 of mouse monoclonal Ab2 TA17A, TA412G or TB310B binding to Ab1 ME361 was determined by preincubating $^{125}$I-labeled monoclonal mouse Ab2 TA17A 30,000 cpm=6 ng/well, TA412G 30,000 cpm=9 ng/well or TB310B 30,000 cpm=7.66 ng/well with various dilutions of rabbit Ab3 sera overnight at 4° C. before adding the mixtures to Ab1 ME361 target (0.06 µg/well). Rabbit sera had been pre-incubated with 400 µg/ml of normal mouse IgG (to block anti-mouse isotypic/allotypic antibodies present in the rabbit sera) before they were added to the $^{125}$I-labeled mouse Ab2 TA17A, TA412G or TB310B. Each Ab3 serum significantly ($p<0.05$) inhibited binding of Ab2 to Ab1 (FIG. 5).

B. Binding of Rabbit Ab3 to Isolated GD2

Sera from each of the two rabbits immunized with Ab2 TA17A Cl2 (#859, #061), Ab2 TA412G Cl1 (#807, #572), or Ab2 TB310B Cl1, (#885, #551) (post-immune sera diluted 1:81) bound significantly ($p<0.01$ as compared to control sera) to isolated GD2 (FIG. 4), but not to GD1a+1b (not shown).

EXAMPLE 4

Delayed-Type Hypersensitivity (DTH) Reaction in Mice

A. Methods

For induction of delayed-type hypersensitivity (DTH) reaction, mice (BALB/c, C57/BL6 and C57/BL6 CD4 knockout mice [McCarrick et al, Transgenic Res., 2:183–190 (1993)], 7 per group) were immunized s.c. with 100 µg of Ab2 (or normal mouse IgG) emulsified in complete Freund's adjuvant.

Immunized mice were challenged with $5\times10^5$ irradiated (400 Gy from caesium source), GD2-positive WM115 melanoma cells in the right ear and $5\times10^5$ irradiated GD2-negative SW1116 colon carcinoma cells in the left ear [D. Herlyn et al, J. Immunother., 15:303–311 (1994)]. Other immunized mice were challenged with 1 µg of purified GD2 antigen in the right ear and 1 µg of purified GD1a+1b antigen (negative control) in the left ear. Ear thickness was measured with a caliper (Poco Test, Mitutoyo, Japan) before and 24, 48, and 72 hr after challenge. Increase in thickness was calculated for each ear at various time points after challenge relative to the thickness before challenge.

B. Results

Figure 6A:
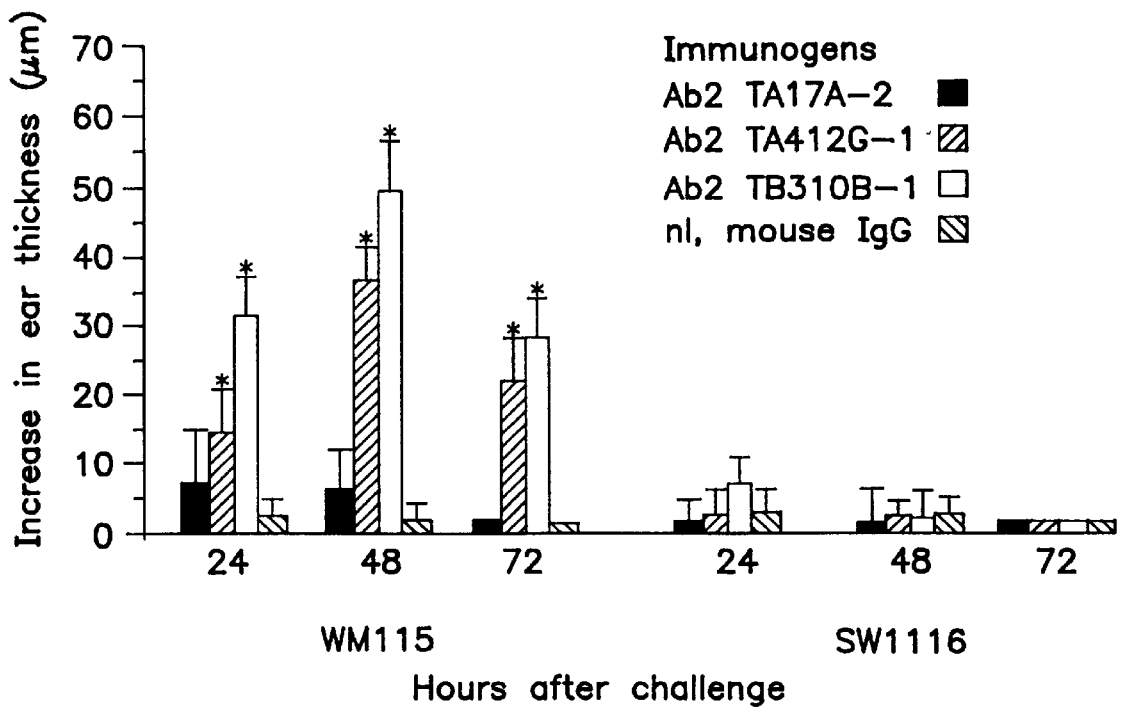
FIG. 6A is bar chart comparing DTH reactions in Ab2-immunized BALB/c mice. The four immunogens were Ab2, TA17A-2, AB2 TA412G-1, AB2 TB310B-1 and normal mouse Ig.

BALB/c mice immunized with Ab2 TA412G or Ab2 TB310B, but not those immunized with Ab2 TA17A-2, raised significant ($p<0.05$) DTH responses against challenges with WM115 melanoma cells as compared to SW1116 CRC cells (FIG. 6A). DTH responses to challenge with the WM115 melanoma cells were significantly ($p<0.01$) higher in mice immunized with Ab2 TA412G or TB310B as compared to normal mouse IgG-immunized ($p<0.01$) mice (FIG. 6A).

Figure 6B:
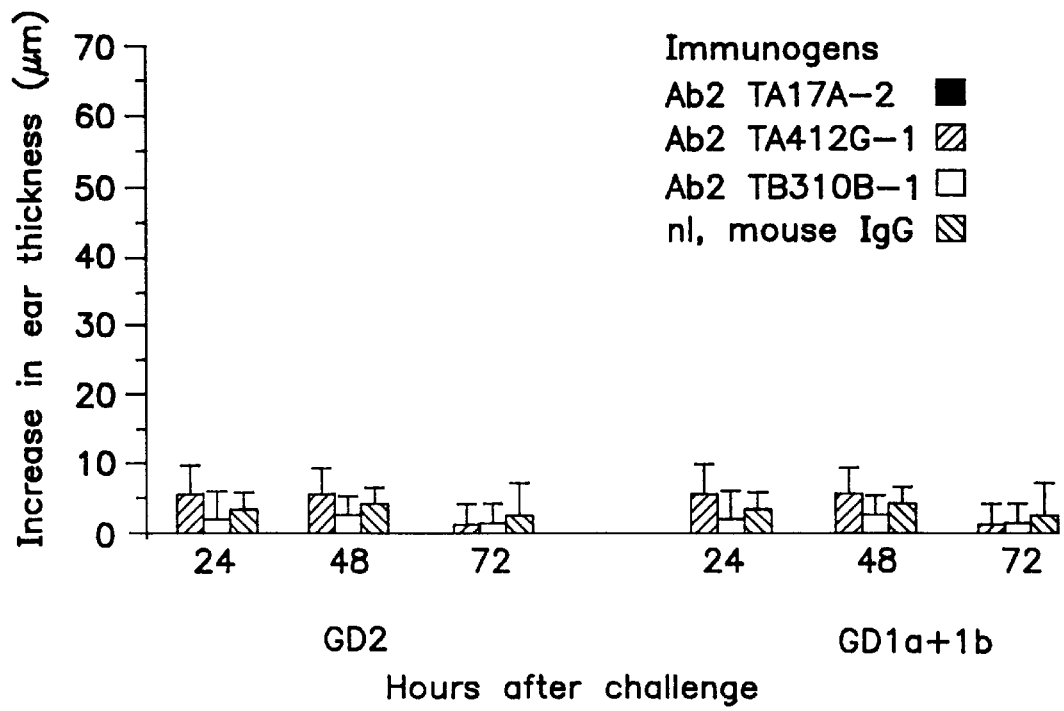
FIG. 6B is a bar chart illustrating absence of DTH reactions in Ab2-immunized BALB/c mice following challenge with GD2 or GD1a and 1b.
Figure 7:
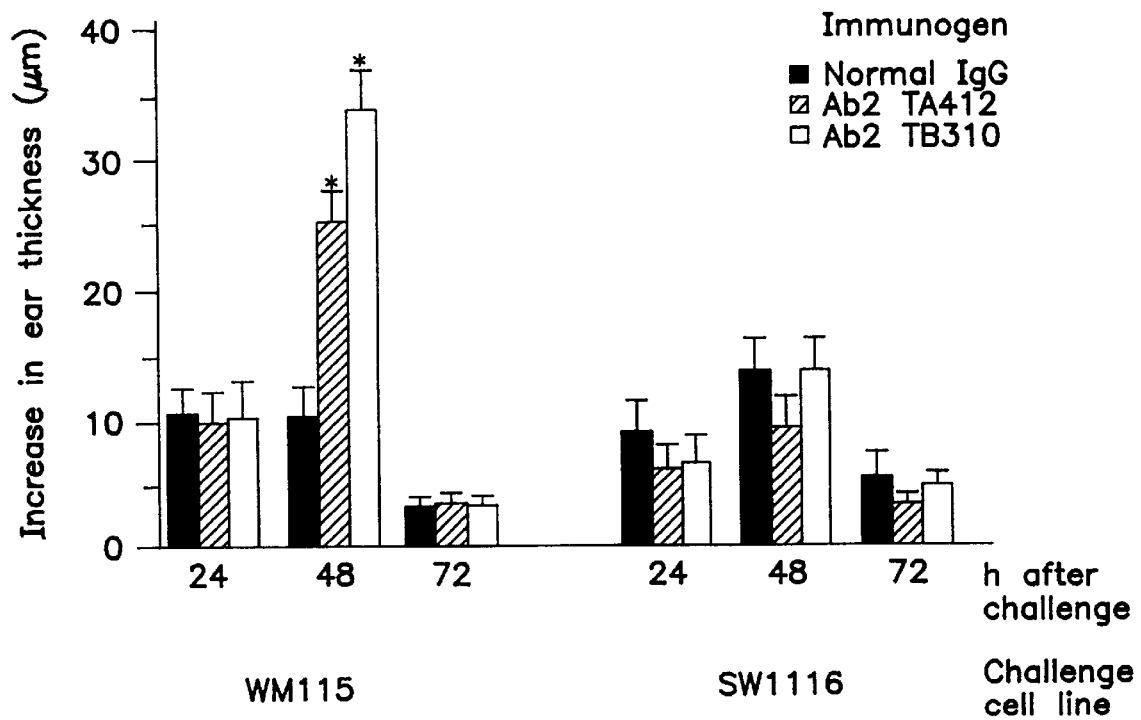
FIG. 7 is a bar chart illustrating DTH induction by Ab2 against Ab1 ME361 in C57/BL6 mice.
Figure 8:
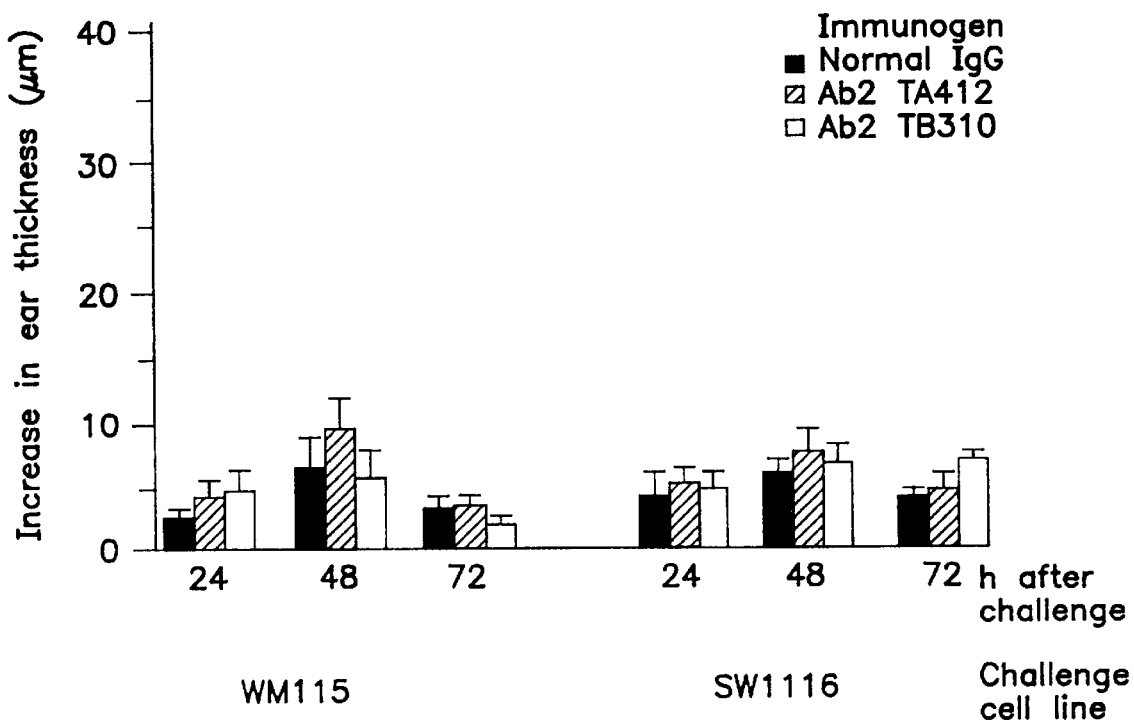
FIG. 8 is a bar chart illustrating the absence of DTH induction by Ab2 against Ab1 ME361 in CD4-knockout mice.

However, Ab2 TA412G or Ab2 TB310B did not induce significant ($p>0.05$) DTH responses to challenges with GD2, as compared to challenges with GD1a+1b and also compared to normal mouse IgG-immunized mice challenged with GD2 (FIG. 6B). Ab2 TA412G and TB310B were also able to elicit DTH responses in normal C57/BL6 mice (FIG. 7), but not in CD4 knockout mice (FIG. 8) suggesting the participation of CD4$^+$ T cells in the DTH reaction.

EXAMPLE 5

Proliferative Lymphocyte Responses in Mice and a Melanoma Patient

A. Mice Studies

For induction of proliferative T-cells, mice were immunized twice s.c. two weeks apart with 75 µg of mouse Ab2 emulsified in complete (first injection) or incomplete (second injection) Freund's adjuvant. Control mice received normal mouse IgG. Two weeks after immunization, mice were sacrificed and lymphocytes from spleen and lymph node were prepared [D. Herlyn et al, J. Immunother., 15:303–311 (1994)]. $5\times10^5$ cells/200 µl/well of splenocytes or lymph node lymphocytes were stimulated with the following: Ab2 or isotype-matched control monoclonal antibody; purified GD2 ganglioside or control GD1a+1b ganglioside [antigens obtained from BioCarb Chemicals, S-22370 Lund, Sweden]; irradiated (100 Gy from cesium source) WM115 melanoma cells [D. Herlyn et al, J. Natl. Cancer Inst., 74:283–289 (1985)] or control SW1116 cells [Koprowski et al, Proc. Natl. Acad. Sci. USA, 75:3405–3409 (1978)]. All tumor cells described were maintained in L-15 media supplemented with 10% fetal calf serum.

All protein stimulants were used absorbed to wells of microtiter plates (10 or 1 µg of protein/well); cells were used in suspension ($10^4$ cells/well). Con A (2 µg/well) was used as positive control stimulant. Lymphocytes were cultured in RPMI 1640 supplemented with 5% fetal calf serum and $5\times10^{-5}$M 2-mercaptoethanol for five days, followed by the addition of 0.5 µCi/well of $^3$H-thymidine overnight. Lymphocytes were then harvested, and counts per minute (cpm) incorporated into the cells were determined in a scintillation counter.

Lymph node lymphocytes, but not splenocytes, from Ab2 TA412G cl.1-immunized mice significantly (p<0.05) proliferated in culture following stimulation of the cells with Ab2 TA412G (10 µg/well), GD2 (10 µg/well) or WM115 cells (10$^4$ cells/well), as compared to the in vitro responses of the lymphocytes from normal IgG immunized mice to stimulation with the same preparations (Table 1).

TABLE 1

Lymphoproliferative Response in Lymph Nodes of Mice Immunized with Ab2 TA412G cl.1
S.I. (means ± S.D. of 4 mice/group)

| Stimulant | | Immunogen | |
|---|---|---|---|
| Code | µg/well | Ab2TA412G cl.1 | normal mouse IgG |
| TA412G cl.1 | 10 | 2.31$^a$ ± 1.32 | 0.41$^a$ ± 0.26 |
| | 1 | 1.40 ± 0.50 | 0.65 ± 0.46 |
| ME313 | 10 | 1.23 ± 0.22 | 1.19 ± 0.19 |
| | 1 | 1.38 ± 0.40 | 1.18 ± 0.19 |
| GD2 | 10 | 3.61$^b$ ± 5.10 | 0.45$^b$ ± 0.20 |
| | 1 | 4.53 ± 7.21 | 0.60 ± 0.28 |
| GD1a + 1b | 10 | 1.27 ± 0.45 | 0.87 ± 0.36 |
| | 1 | 0.77 ± 0.54 | 0.90 ± 0.10 |
| WM115 | 10$^{4*}$ | 36.47$^c$ ± 41.03 | 2.20$^c$ ± 0.53 |
| SW1116 | 10$^{4*}$ | 2.43 ± 1.58 | 1.91 ± 0.52 |

* cells/well
$^{a-c}$ Values with identical letters differ significantly (p < 0.05 or less) from each other.

In contrast, there was no difference between the lymphoproliferative responses of Ab2 and normal IgG-immunized mice after stimulation of the lymphocytes with control preparations (MAb ME313, GD1a+1b, SW1116 cells). Although proliferative responses of the lymphocytes from Ab2 TA412G cl.1-immunized mice to stimulation with the Ab2, GD2, or WM1115 cells seem to be higher as compared to stimulation with the corresponding control preparations (see Table I), the test does not allow for comparison of variables obtained from mice within the same group. Furthermore, when the experimental (Ab2 immunized group) and control values (normal Igb-2 immunized group) were compared by student's t-test, they did not differ significantly, presumably because of the relative high standard deviations of the means and the small number of mice included per group. Neither splenocytes nor lymph node cells from Ab2 TB310B-immunized mice showed significant proliferation after stimulation of the cells with Ab2, antigen or antigen-positive cells.

B. Melanoma Patient

To determine whether the Ab2 can stimulate cultured lymphocytes from a melanoma patient, tumor infiltrating lymphocytes (TIL) from a spleen metastases of primary melanoma or Ficoll-purified peripheral blood mononuclear cells (PBMC) were stimulated with various protein or cell preparations as described for murine lymphocytes (see above), except that autologous melanoma cells WM3122 were used as cellular and PHA (2 µg/well) as positive control stimulants. [The WM3122 melanoma cell line was established from the spleen metastases of a patient. ] Replicate lymphocyte cultures were restimulated with the various preparations for an additional five days before $^3$H-thymidine was added to the wells. Results are presented as stimulation index (S.I.):

S.I.=cpm (with stimulant)/cpm (with buffer)

TIL from patient #3122 showed significant proliferation after secondary, but not primary, stimulation with Ab2 TA412G (10 µg/well) or Ab2 TB310B (10 or 1 µg/well) as compared to stimulation with control MAb ME313 (Table 2). PBL from patient #3122 also showed significant proliferation to stimulation with GD2 (p<0.01), or WM3122 cells (p<0.05) as compared to stimulation with the appropriate control preparations (Table 2).

TABLE 2

Lymphoproliferative Responses to Stimulation with Ab2 or Antigen in PBL from Patient WM3122

| Stimulant | | |
|---|---|---|
| Code | µg/ml | S.I. (means ± S.D.) |
| TA412G cl.1 | 10 | 1.75 ± 0.14 |
| | 1 | 3.47$^b$ ± 0.22 |
| TB310B cl.1 | 10 | 4.94$^b$ ± 0.34 |
| | 1 | 2.19$^b$ ± 0.05 |
| ME313 (control) | 10 | 1.53 ± 0.04 |
| | 1 | 1.22 ± 0.06 |
| Normal Mouse IgG (control) | 10 | 1.20 ± 0.15 |
| | 1 | 1.15 ± 0.13 |
| GD2 | 10 | 4.01$^b$ ± 0.34 |
| | 1 | 1.53 ± 0.10 |
| GD1a + 1b | 10 | 1.53 ± 0.08 |
| | 1 | 1.28 ± 0.07 |
| WM3122 | 10$^{4c}$ | 2.65$^b$ ± 0.35 |
| SW1116 (control) | 10$^{4c}$ | 2.00 ± 0.09 |
| PHA | 2 | 49.50 ± 1.98 |

$^a$ Primary stimulation.
$^b$ Values are significantly different (p < 0.05 – < 0.01) from the corresponding control value.
$^c$ Number of cells/well.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A hybridoma cell line TA17A C12, having the ATCC Accession Number HB-12083.

2. A hybridoma cell line TA412G Cl1, having the ATCC Accession Number HB-12084.

3. A hybridoma cell line TB310B Cl1, having the ATCC Accession Number HB-12085.

4. A murine anti-idiotype antibody TA17A Cl2 having the ability to mimic GD2 function.

5. A murine anti-idiotype antibody TA412G Cl1 having the ability to mimic GD2 function.

6. A murine anti-idiotype antibody TB310B Cl1 having the ability to mimic GD2 function.

7. A recombinant antibody comprising a functional fragment containing the antigen binding site of a murine anti-idiotypic antibody selected from the group consisting of TA17A Cl2, TA412G Cl1, and TB310B Cl1.

8. The recombinant antibody according to claim 7, which is selected from the group consisting of a bifunctional antibody, a chimeric antibody, and a humanized antibody.

9. An immunogenic composition that elicits a CD4-mediated cellular immune response, said composition comprising a pharmaceutically acceptable carrier and an anti-idiotype antibody selected from the group consisting of (a) TA17A Cl2, (b) TA412G Cl1, (c) TB310B Cl1, and (d) a recombinant antibody comprising a functional fragment containing the antigen binding site of anti-idiotypic antibody (a), (b), or (c).

10. The composition according to claim 9 wherein said composition further comprises alum.

11. The recombinant antibody according to claim 7, comprising the complementarity determining regions (CDRs) of murine anti-idiotype antibody TA17A Cl1.

12. The recombinant antibody according to claim 7, comprising the complementarity determining regions (CDRs) of murine anti-idiotype antibody TA412G Cl1.

13. The recombinant antibody according to claim 7, comprising the complementarity determining regions (CDRs) of murine anti-idiotype antibody TB310B Cl1.

14. A functional fragment of murine anti-idiotype antibody TA17A Cl2, wherein the fragment is selected from the group consisting of Fab, $F_v$, and $F(ab')_2$.

15. A functional fragment of murine anti-idiotype antibody TA412G Cl1, wherein the fragment is selected from the group consisting of Fab, $F_v$, and $F(ab')_2$.

16. A functional fragment of murine anti-idiotype antibody TB310B Cl1, wherein the fragment is selected from the group consisting of Fab, $F_v$, and $F(ab')_2$.

17. The immunogenic composition according to claim 9, wherein the recombinant antibodies comprises a functional fragment is selected from the group consisting of a Fab, $F_v$, and $F(ab')_2$.

18. The immunogenic composition according to claim 9, wherein the recombinant antibody comprises the complementarity determining regions (CDRs) of the selected anti-idiotype antibody (a), (b) or (c).

19. An immunogenic composition comprising a pharmaceutically acceptable carrier and a functional fragment of a murine anti-idiotype antibody selected from the group consisting of TA17A Cl2, TA412G Cl1, and TB310, wherein said functional fragment is selected from the group consisting of Fab, $F_v$, and $F)(ab')_2$.

* * * * *